United States Patent [19]

Wolfbeis et al.

[11] Patent Number: 4,716,118
[45] Date of Patent: Dec. 29, 1987

[54] METHOD FOR DETERMINING IONIC STRENGTH OF A SAMPLE

[75] Inventors: Otto S. Wolfbeis; Helmut Offenbacher, both of Graz, Austria

[73] Assignee: AVL AG, Schaffhausen, Switzerland

[21] Appl. No.: 898,804

[22] Filed: Aug. 21, 1986

Related U.S. Application Data

[63] Continuation of Ser. No. 640,881, Aug. 15, 1984, abandoned.

[30] Foreign Application Priority Data

Aug. 26, 1983 [AT] Austria .................................. 3061/83

[51] Int. Cl.$^4$ ..................... G01N 21/77; G01N 33/52
[52] U.S. Cl. ......................................... 436/2; 422/56; 436/163; 436/169; 436/172
[58] Field of Search ................... 436/2, 163, 164, 169, 436/172; 422/56, 57; 73/32 R

[56] References Cited

U.S. PATENT DOCUMENTS

| | | | |
|---|---|---|---|
| 3,926,830 | 12/1975 | Horiguchi et al. | 436/163 X |
| 4,029,598 | 6/1977 | Neisius et al. | 436/163 |
| 4,166,804 | 9/1979 | Bleha et al. | 436/163 |
| 4,318,709 | 3/1982 | Falb et al. | 422/57 X |
| 4,376,827 | 3/1983 | Stiso et al. | 436/2 |
| 4,473,650 | 9/1984 | Wang | 436/163 X |
| 4,511,660 | 4/1985 | Lubbers et al. | 436/163 |
| 4,532,216 | 7/1985 | Wang | 436/2 |

FOREIGN PATENT DOCUMENTS 2944980 5/1980 Fed. Rep. of Germany .
3343636 6/1984 Fed. Rep. of Germany .

OTHER PUBLICATIONS

Harper, Analytical Chemistry, vol. 47, No. 2, pp. 348-351, Feb. 1975.
Chemical Abstracts, vol. 93, No. 93:217593a (1980), Falb et al.

Primary Examiner—Barry S. Richman
Assistant Examiner—Robert J. Hill, Jr.
Attorney, Agent, or Firm—Watson, Cole, Grindle & Watson

[57] ABSTRACT

One measurement each is obtained from two optical sensors of ion concentration, following which the measured values are used for empirical determination of the ionic strength of an electrolytic solution. The sensors contain the same indicator substance but differ with regard to surface modification, thus ensuring different responses to ionic strength in spite of identical excitation and fluorescence wavelengths and the resulting simplicity of the optical system.

2 Claims, 8 Drawing Figures

METHOD FOR DETERMINING IONIC STRENGTH OF A SAMPLE

This application is a continuation of application Ser. No. 640,881, filed Aug. 15, 1984, now abandoned.

BACKGROUND OF THE INVENTION

This invention relates to a method for determining the ionic strength of an electrolytic solution and to measuring equipment for implementing this method.

DESCRIPTION OF THE PRIOR ART

The ionic strength J of a solution is defined by equation (1):

$$J = \tfrac{1}{2} \sum_i c_i z_i^2 \qquad (1)$$

where
J denotes ionic strength,
$c_i$ denotes concentration of ions of type i, and
$z_i$ denotes charge of ions of type i.

For determination of the ionic strength it is therefore necessary to measure the concentration of the individual types of ions and to calculate the ionic strength according to (1), using standard tables of the electrochemical valences of the individual electrolytic components.

For a number of problems of measurement and interpretation it will be sufficient to determine the ionic strength in this manner. However, in biological systems, e.g., in metabolic processes, changes over time of the material composition of the electrolyte will occur frequently, resulting in a change of J. For calculation of the respective ionic strength, the time-consuming method of determining the individual electrolytic components, as well as their concentrations and valences, and of the subsequent calculation of J, will not be possible in the given time.

The ionic strength may also be determined by experiment, i.e. by measuring the mean activity coefficients of the components of the electrolytic solution. According to DEBYE-HÜCKEL, the mean activity coefficient of the solution components is given by equation (2):

$$-\lg f_\pm = A \cdot z_+ \cdot |z_-| \cdot \sqrt{J} \qquad (2)$$

where
$f_\pm$ = mean activity coefficient,
$A = 0.5093\ (M^{-1})^{\frac{1}{2}}$ for $H_2O$ at 298.15K, and
$z_+, z_-$ = absolute charge of positive or negative ions, with the symbol M indicating concentration (molar), i.e., the amount of a substance (in mol) per liter solution, $$M = \frac{\text{mol}}{\text{liter}}.$$

This theoretical law (2) is a limit law and may only be applied to diluted systems of electrolytes.

Furthermore, a set-up and method of determination of the ionic strength of liquid samples are described in German laid open print No. 29 44 980, and in the corresponding reference in Chem. Abstr. 93, 21 75 93 (1980), in which filter paper is impregnated with a solution of a polymeric polyelectrolyte (for instance, a copolymer of maleic acid and methyl vinyl ether) at a pH of 8, and is dried and subsequently colored with bromothymol blue and then dried again. The paper strip obtained in this way is dipped into the sample (e.g. urine); after about 60 seconds the resulting change in color of the indicator is measured by means of a reflection photometer. The disadvantage of this method is that measurement and evaluation take a comparatively long time, making them suitable only for the testing of slow changes in ionic strength, and only in retrospect.

SUMMARY OF THE INVENTION

It is an object of the present invention to provide a method and a device for implementing this method which will permit simple and direct measurement of ionic strength and its changes over time.

According to the invention this is achieved by separately measuring ionic concentration with two optical sensors which contain the same indicator but differ with regard to surface modification—thus responding differently to the ionic strength of the electrolyte solution—and by empirically inferring the ionic strength from the difference in the measured values obtained by the two sensors.

Although this method will basically permit the ionic concentration of any ions suitable for measurement by optical indicators to be used for obtaining the two measurement values required for finding the difference, the use of fluorescence-optical pH sensors or rather of the respective values measured for the concentration of hydrogen ions, will be of particular advantage. This will also enable the pH value to be determined at the same time as the ionic strength, which is often useful.

It is general knowledge that the measured dissociation constant of an indicator will vary with the ionic strength of the solution due to a shifting of the activity coefficients. The change of the $pK_a$ value measured increases with an increase of the charge of the indicator. In this context the $pK_a$ values are the negative (base 10) logarithms of the dissociation constants of an acid.

$$pK_a = -\log K$$

This notation has been chosen in formal analogy to the pH values. The dissociation constant K is defined as $$K = \frac{[H^+][\text{anion}]}{[\text{H-anion}]}$$

$[H^+]$ being the concentration of free hydrogen ions, [anion] the concentration of the corresponding anion, and [H-anion] the concentration of the non-dissociated complex.

The difference between the values obtained from a sensor ($M_1$) being largely independent of ionic strength and another sensor ($M_2$) being dependent on ionic strength, thus is a function of the ionic strength J of the solution.

$$M_1 - M_2 = f(J) \qquad (3)$$

This function may be of considerable complexity, depends on the type and manufacture of the sensors, and must be found empirically for each individual sensor combination (see FIGS. 1 and 5, for example).

This relationship is best obtained by using measurements of defined samples and evaluating them in a computer, which should also be used for evaluation of the solutions to be tested.

When pH fluorescence indicators are immobilized on glass surfaces it has been found that a chemical surface modification may be utilized to produce pH sensors which are either largely independent of or largely dependent on ionic strength.

BRIEF DESCRIPTION OF THE DRAWINGS

Further characteristics and advantages of the invention are described below, with reference to the embodiments and diagrams and schematic formulae contained in the enclosed drawings, in which.

DETAILED DESCRIPTION OF THE PREFERRED EMBODIMENTS

Figure 1:
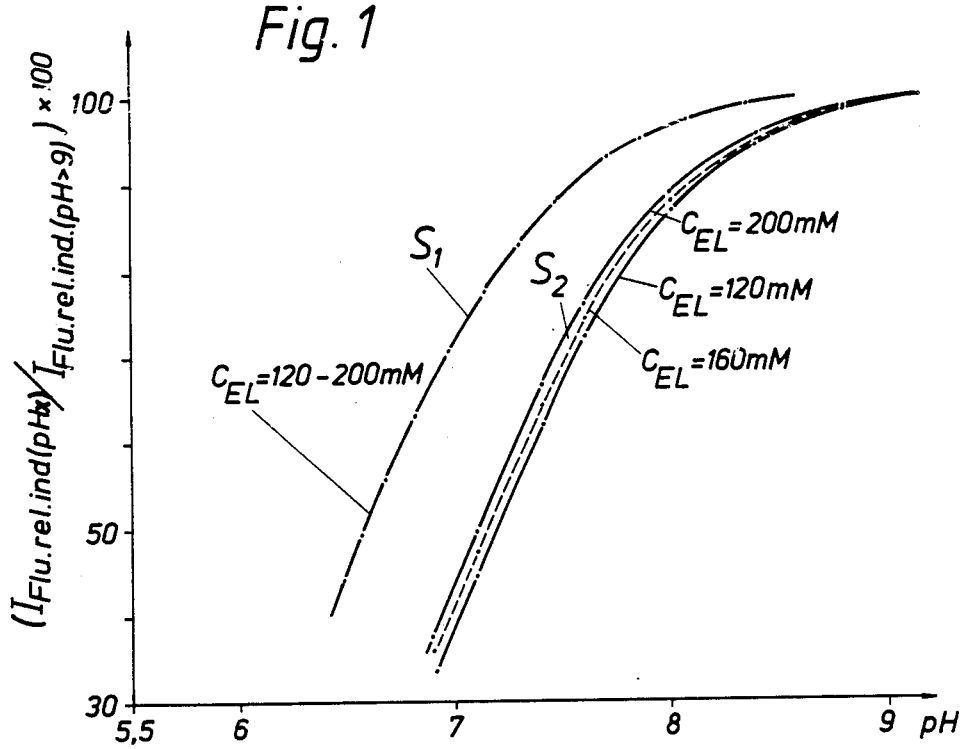
FIG. 1 shows the variation with ionic strength of the pH value/fluorescence intensity relation of a measuring device according to the invention.

FIG. 1 presents pH titration curves of a sensor whose indicator environment was modified chemically in two different ways after the indicator had been immobilized on glass ($C_{EL}$ stands for concentration of the electrolyte, and $I_{flu.rel.ind.}$ for the relative fluorescence intensity of the indicator anion). This process accounts for the minimal dependency on ionic strength of sensor $S_1$ and the extreme J-dependency of sensor $S_2$, although the immobilized indicator substance used was identical for both sensors. FIG. 1 shows that the pH value measured by sensor $S_1$ is independent of ionic strength over a wide range ($C_{EL}$=120–200 mM), whereas the pH value indicated by sensor $S_2$ is strongly dependent in ionic strength. The ionic strength may therefore be inferred from the difference between measured and anticipated pH value as obtained from sensor $S_2$. The relationship between deviation of pH measurement and ionic strength which must be found empirically (equation (3)) will permit determination of the ionic strength in the pH range of $pK_a$ (sensor $S_2$)±0.4. In practice, the measurement is performed by measuring the pH value of a solution with two sensors of different surface modification, one of these sensors being largely independent with regard to J, whereas the other one shows a marked dependency.

Suitable indicators lending themselves for pH measurement in their immobilized form are described, e.g., in *Handbook of Chemistry and Physics*, 55th edition (1974/75), p. D115, and in Fres. Z. Anal. Chem., vol. 314, p. 577 (1983).

The method described by the invention is of particular advantage as it does not employ two different indicator substances with two different excitation and fluorescence wavelengths for the measurement of J by the above relationship which is to be found empirically (equation (3)), and therefore avoids the difficulties of spectral discrimination of overlapping excitation and fluorescence bands. For this method one indicator substance with only one excitation and fluorescence wavelength will be sufficient, which will result in a much simpler optical system.

Suitable indicators may include both absorption and fluorescent dyes dependent on ionic concentration; for pH measurements, indicators are used whose $pK_a$ values are in the vicinity of the pH range to be measured. For physiological liquids, indicators with $pK_a$ values from 6.5 to 8.0 are best.

The method described by the present invention may therefore be used to advantage both for pH indication (or rather, ionic concentration in general) and for one-time or continuous determination of ionic strength.

Figure 5:
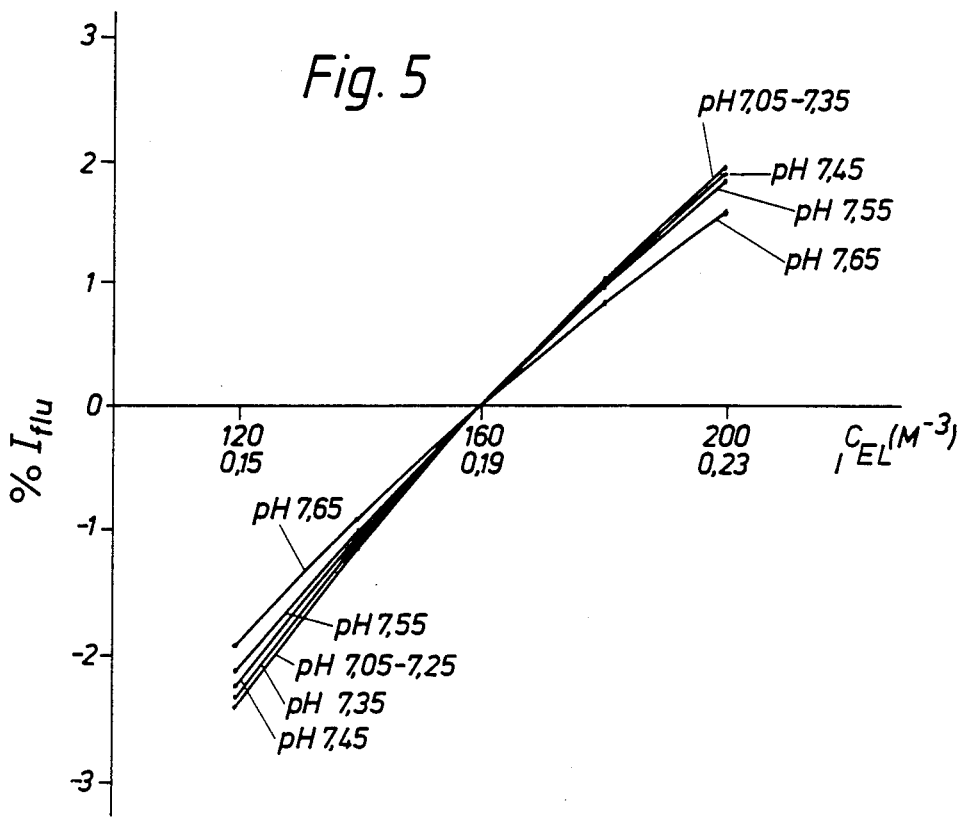
FIG. 5 shows the relative variation in fluorescence at different pH values, depending on the concentration of the electrolyte.
Figure 6:
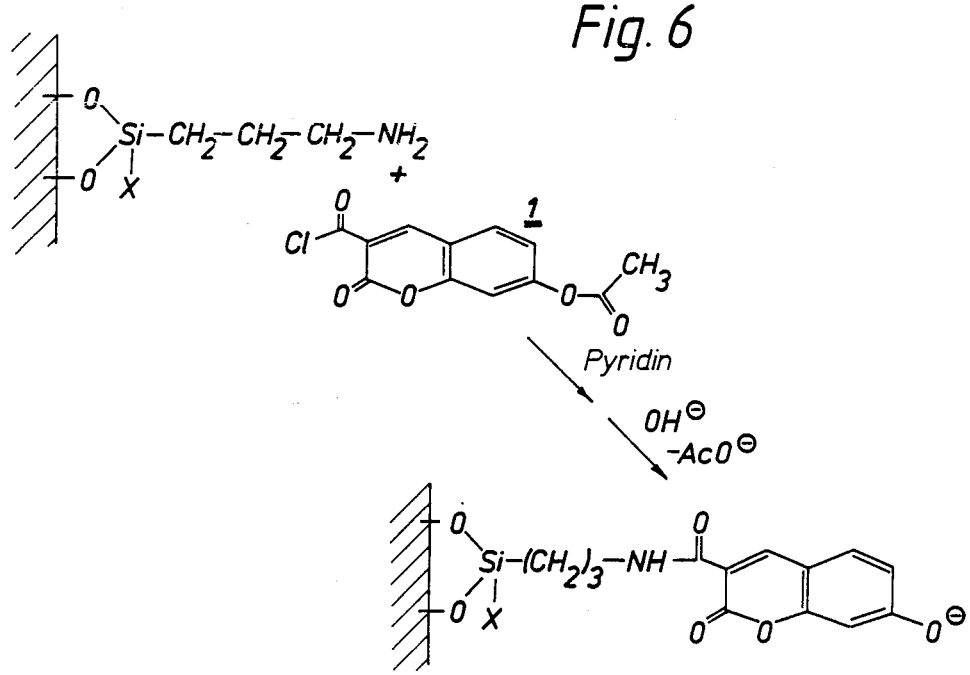
FIG. 6 is a schematic formula for example I.

According to another characteristic of the invention, a measuring device for implementation of the above method comprises a sample chamber into which the electrolyte solution to be measured is fed and an optical measuring unit which may be brought into contact with the sample at least indirectly, and is designed such that the measuring unit carries two optical ion concentration sensors, especially pH sensors, containing the same indicator substance whose surface is modified however, by embedding the indicator in different microenvironments, such that the respective ion concentration values, especially $pK_a$ values, will depend on the ionic strength in different degrees (FIGS. 5 and 6).

An enhanced variant of the invention provides that one of the two sensors has a high local concentration of positive or negative charge carriers in the area containing the indicator, while for the other sensor this concentration is low to negligible.

Figure 2:
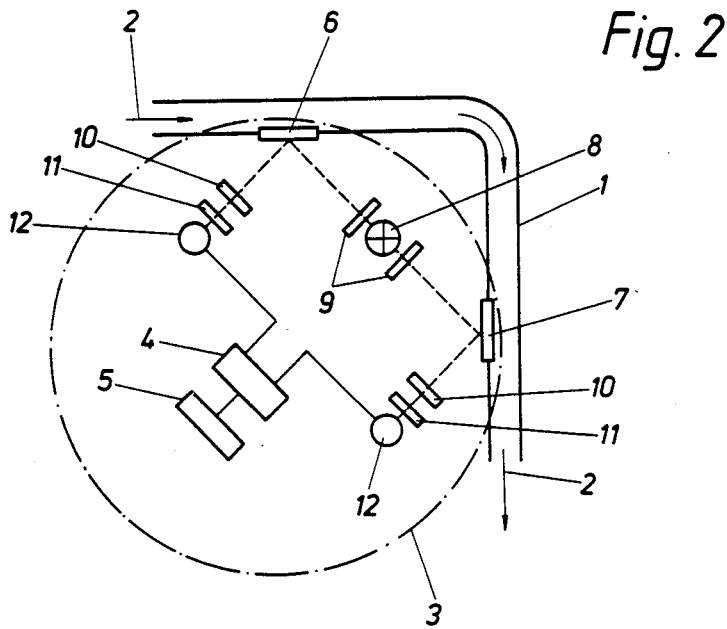
FIG. 2 is a diagram of a measuring device according to the invention, FIGS. 3a, b, c and 4 each show a schematic formula of a typical chemical reaction used for embedding the indicator substance of a sensor for a device according to the invention.

The sensors are produced, e.g., by chemical coupling of the indicator substance to the surface of a polymer carrier material. Suitable carriers are organic polymers as well as glass and other inorganic materials. Fluorescence-optical indicators are of advantage as they will also permit the measuring of cloudy liquids by means of remission techniques (FIG. 2).

Because of its optical transparency and mechanical stability, glass is preferably used as a carrier material. The best pH indicators are 7-hydroxycumarine and hydroxypyrene trisulphonate. By immobilizing (chemically bonding) such indicators to glass substrates, pH sensors of mechanical stability and surface fluorescence are achieved.

Such sensors will depend on ionic strength and will show various unexpected surface effects, however. In order to eliminate these effects and to achieve a uniform environment with regard to ionic strength, the surface of the carrier material must undergo further chemical modification. If glass is used as a carrier, this is achieved by selecting the reagents such that they render the glass surface hydrophobic and introduce a high density of ionic groups into the indicator environment. In this way the indicator substance is surrounded by a high local concentration of ions (e.g. ammonium groups), and the change in ionic strength effected by the sample will remain comparatively small.

Figure 3:
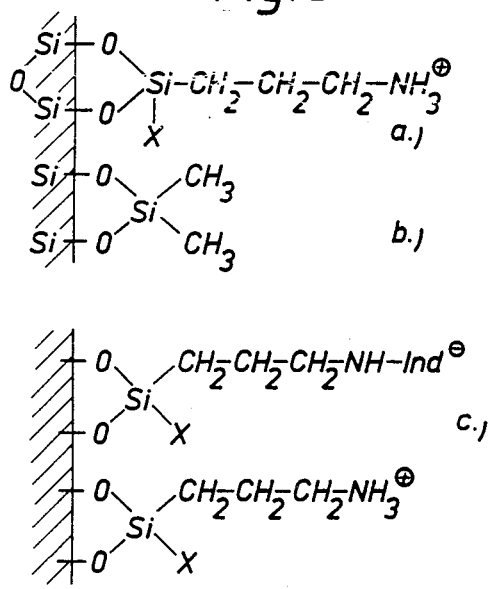
Figure 4:
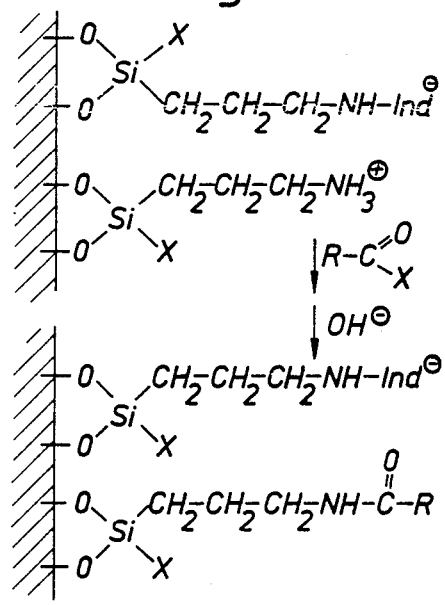

Aminopropyl triethoxysilane and dichlorodimethylsilane have proved to be suitable reagents. The former is used mainly for obtaining high concentrations of ammonium ions in the vicinity of the chemically immobilized pH indicators of the glass surface at physiological pH values (FIG. 3a). This will also ensure a charge compensation of the indicator which usually is charged negatively. The other reagent (dichlorodimethylsilane) is used for blocking the silicate anions remaining on the glass surface (FIG. 3b), thus preventing any further interaction with the indicator ion. At the same time the glass surface is made water-repellent. This process will permit the pH indicator to be embedded into a well defined environment whose ionic strength is largely constant (FIG. 3c). If the ammonium groups are finished with an acid anhydride or an acid chloride, an amide will form which can no longer carry a charge (FIG. 4). This will remove the charge compensation and the $pK_a$ value of the indicator will become strongly dependent on ionic strength. By comparison of the pH values of an electrolyte solution obtained from the two sensors the ionic strength may thus be calculated according to equation (3).

FIG. 5 shows the fluorescence intensity $I_{flu}$ relative to the total anion fluorescence in percent at various pH values, plotted against the variation of the electrolyte concentration $C_{EL}$ in the range of 160±40 mM/l (NaCl+0.033M phosphate buffer). It can be clearly seen here that for pH values in the range of ±0.4 of the $pK_a$ value of the indicator relative to a gauge curve obtained for pH=$K_a$ (ind.), the maximum error of measurement is 0.002. For pH values outside of this range the error will increase rapidly. As an indicator immobilized 7-hydroxycumarine was used, as is described in the following example.

EXAMPLE I

A pH fluorescence sensor based on 7-hydroxycumarine (cf. also FIG. 6):

Glass slides sized 2×2 cm are modified—in some cases after a surface increase—by activating them for two hours in a 1:1 mixture of sulphuric acid and nitric acid, following which they are rinsed with water and dried for twelve hours over $P_4O_{10}$. They are then heated at reflux for one hour in a 0.01% solution of 3-aminopropyl triethoxysilane (EGA-Chemie) in toluene with a content of 0.01% water and 0.001% tosyl chloride. The glass slides obtained in this manner carry free amine groups on their surfaces. They are dried with the use of a drying agent for twelve hours at 120° C., and subsequently cooked at reflux in dichlorodimethylsilane for 48 hours. The water-repellent glass carriers obtained in this way are then reacted with 7-acetoxycumarine-3-carboxylic acid chloride in the presence of pyridine (1 in FIG. 6). As some of the amine groups will not react with the indicator acid chloride, a sufficient number of amine groups will remain on the glass surface which are protonated in the physiological pH range. The sensors obtained by this procedure will show a negligible dependency on ionic strength ($\leq \pm 0.003$ pH units at a variation of the electrolyte concentration from 120 to 200 mM).

If these sensors are treated with acid chlorides or acid anhydrides, the sensors obtained after hydrolysis of the indicator-protecting group will be strongly dependent on ionic strength ($\pm 0.035$ pH units at a variation of the electrolyte concentration from 120-200 mM).

EXAMPLE II

Figure 7:
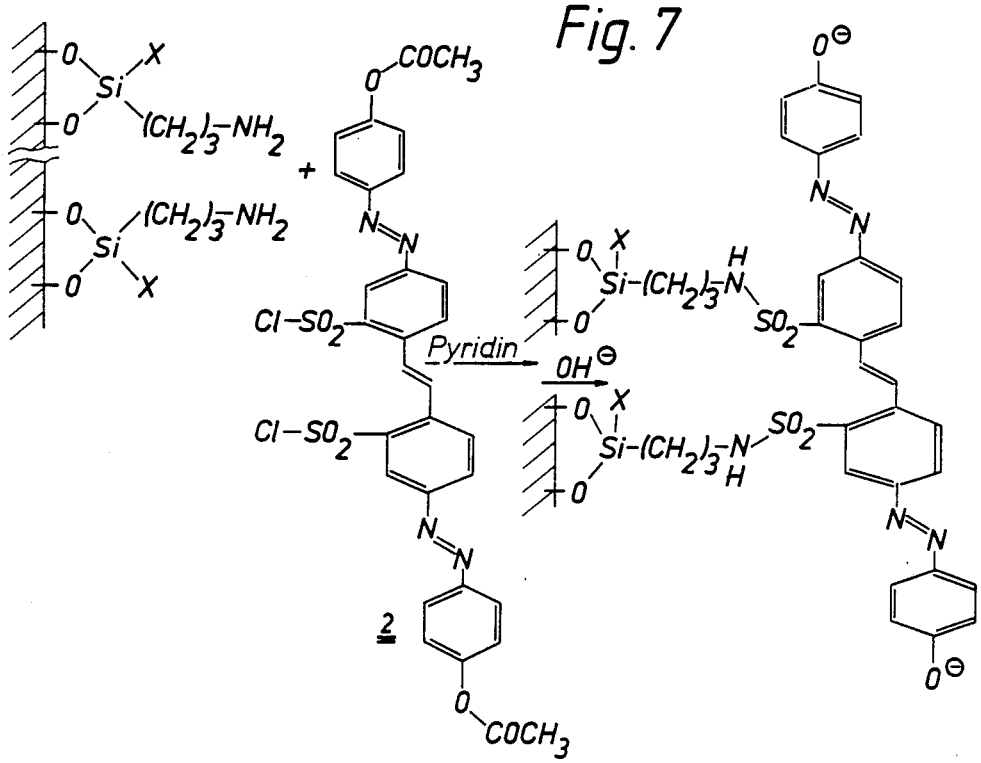
FIG. 7 is a schematic formula for example II.

A pH sensor based on an absorption indicator obtained by immobilization of 4,4'-di(p-hydroxyphenyldiazo)transstilbene-2,2'-disulphonic acid (cf. also FIG. 7):

As in Example I, the surfaces of the glass carriers are chemically modified. The dye which is commercially available in form of its sodium salt, is cooked with acetic anhydride for the purpose of immobilization in dimethyl formamide, and the resulting acetate is converted into the protected acid dichloride (2 in FIG. 7) by gently heating it with phosphorus pentachloride. Bonding to the glass carrier is best performed in the presence of pyridine and in the absence of water. The indicator acetate is saponified by simply dipping the slides into a pH-10-buffer. The strong dependency on ionic strength is achieved by finishing the sensors with acetic anhydride, as in the case of the pH fluorescence sensors in Example I.

The variant of a measuring device for implementation of the described method for determining the ionic strength of an electrolytic solution, which is presented in FIG. 2, essentially comprises a sample chamber designed as a throughgoing pipe 1, through which the electrolyte solution to be measured will flow in the direction of arrows 2, and an optical measuring unit 3 which may be brought into contact with the sample at least indirectly and which is connected to an evaluation unit 4 and a display unit 5 connected thereto.

The measuring unit 3 is provided with two ion concentration sensors 6,7, of which sensor 6, for example, is made largely independent of the respective ionic strength prevailing in the sample, in a manner described above, whereas the ion concentration value obtained from sensor 7 will depend on the prevailing ionic strength.

Via a light source 8 preceded by filters 9, the sensors 6,7, which are in contact with the sample, may be excited to give off fluorescent light which is registered by detectors 11 after having passed through filters 10. The detectors 11 are connected via amplifiers 12 to the evaluation unit 4 in which the ionic strength of the electrolytic solution is calculated from the differing measurement values of sensors 6,7, for instance by means of a computer (not shown here), using the empirically found relationship referred to in equation (3). The value measured in this way may be displayed in the display unit 5, or it may be further processed in a manner not shown here.

In this set-up one of the main benefits of the present invention is made evident, i.e., the use of one common source of excitation light for the sensors 6,7 carrying identical indicator substances, and of identical detectors for the fluorescent light.

Thus the device presented in this drawing, together with the sensors discussed before, will enable the ionic strength of the electrolytic solution to be measured in a simple and direct manner.

Figure 8:
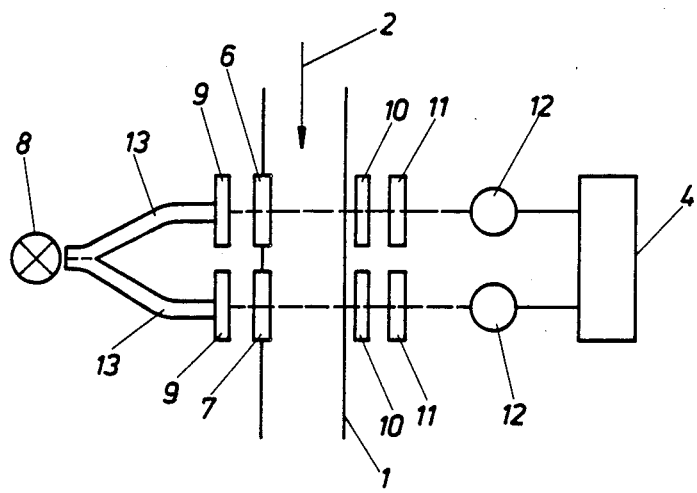
FIG. 8 shows another variant of a measuring device according to the invention.

The variant shown in FIG. 8 differs from that in FIG. 2 mainly by its use of a transmitted light technique; via optical fibres 13 and filters 9 the light-source 8 again illuminates two sensors 6,7 which will respond in different ways to the ionic strength of the electrolytic solution flowing through the sample pipe 1 along arrow 2, and whose fluorescent light—after passing through filter 10—will be received by detectors 11 located opposite the sensors. The detectors 11 again are connected with amplifiers 12 and the evaluation unit 4; evaluation and display of the measured values are performed as discussed above.

Although not shown in the variants according to FIGS. 2 and 8, the proposal has been made that a reference sensor be mounted in addition to the two sensors for ionic concentration, which would eliminate the influence of intensity fluctuations of the excitation light, and would further increase measuring accuracy. Besides, it would be possible to use absorption sensors instead of fluorescence sensors, provided that there is a difference in dependency between values and ionic strength.

We claim:

1. A method for determining an ionic strength value of an electrolytic solution having a certain ionic concentration, said method comprising the steps of
   (a) providing two identical carrier materials, each of said two carrier materials comprising glass and having a carrier surface,
   (b) treating said carrier surface of each of said two carrier materials with aminopropyl triethoxysilane and dichlorodimethylsilane to obtain high concentrations of ammonium groups on each of said carrier surfaces and block any silicate anions remaining on each of said carrier surfaces,
   (c) providing a pH indicator substance,
   (d) chemically coupling said indicator substance to said treated carrier surface of each of said two carrier materials,
   (e) chemically modifying the carrier surface of at least one of said two carrier materials to which said indicator substance has been chemically coupled in step (d) by treatment with an acid chloride so as to provide the carrier surface of one of said two carrier materials with a different microenvironment than the carrier surface of the other of said two carrier materials, thus providing two optical sensors which will respond differently to the ionic strength value of said electrolytic solution,
   (f) measuring the pH of said electrolytic solution using said two optical sensors, thus obtaining two differing pH measurement values,
   (g) calculating a difference between said two differing pH measurement values obtained in step (f), and
   (h) empirically inferring the ionic strength value of said electrolytic solution from said difference calculated in step (g).

2. A method for determining an ionic strength value of an electrolytic solution having a certain ionic concentration, said method comprising the steps of
   (a) providing two identical carrier materials, each of said two carrier materials comprising glass and having a carrier surface,
   (b) treating said carrier surface of each of said two carrier materials with aminopropyl triethoxysilane and dichlorodimethylsilane to obtain high concentrations of ammonium groups on each of said carrier surfaces and block any silicate anions remaining on each of said carrier surfaces,
   (c) providing a pH indicator substance,
   (d) chemically coupling said indicator substance to said treated carrier surface of each of said two carrier materials,
   (e) chemically modifying the carrier surface of at least one of said two carrier materials to which said indicator substance has been chemically coupled in step (d) by treatment with an acid anhydride so as to provide the carrier surface of one of said two carrier materials with a different microenvironment than the carrier surface of the other of said two carrier materials, thus providing two optical sensors which will respond differently to the ionic strength value of said electrolytic solution,
   (f) measuring the pH of said electrolytic solution using said two optical sensors, thus obtaining two differing pH measurement values,
   (g) calculating a difference between said two differing pH measurement vlaues obtained in step (f), and
   (h) empirically inferring the ionic strength value of said electrolytic solution from said difference calculated in step (g).

* * * * *